United States Patent [19]
Chamberlain et al.

[11] Patent Number: 6,051,562
[45] Date of Patent: *Apr. 18, 2000

[54] STABILIZATION AND USE OF HETEROGENEOUS LIQUID COMPOSITIONS

[75] Inventors: Peter Chamberlain; Eleanor Harden, both of West Yorkshire, United Kingdom

[73] Assignee: Ciba Specialty Chemical Water Treatment Limited, West Yorkshire, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/617,823

[22] PCT Filed: Sep. 15, 1994

[86] PCT No.: PCT/GB94/02014

§ 371 Date: Apr. 8, 1996

§ 102(e) Date: Apr. 8, 1996

[87] PCT Pub. No.: WO95/07613

PCT Pub. Date: Mar. 23, 1995

[30] Foreign Application Priority Data

Sep. 15, 1993 [GB] United Kingdom ............. 9319112

[51] Int. Cl.⁷ ............. A01N 57/08; A61K 7/40; C08J 3/03
[52] U.S. Cl. ............. 514/89; 424/401; 524/521; 524/522; 524/523; 516/67; 516/73
[58] Field of Search ............. 252/312; 514/89, 514/772.2, 772.4, 772.6, 788.1, 938, 939, FOR 10; 71/64.08; 516/72, 73, 67; 504/116; 524/803, 503, 521, 522; 424/401

[56] References Cited

U.S. PATENT DOCUMENTS

| | | | |
|---|---|---|---|
| 4,071,617 | 1/1978 | Graves et al. | 504/116 |
| 4,303,642 | 12/1981 | Kangas | 424/772.6 |
| 4,472,291 | 9/1984 | Rosano | 252/312 |
| 4,798,682 | 1/1989 | Ansmann | 252/312 |
| 4,966,621 | 10/1990 | Heinrich et al. | 71/86 |
| 4,997,642 | 3/1991 | Curtis et al. | 71/64.08 |
| 5,194,263 | 3/1993 | Chamberlain et al. | 504/347 |
| 5,321,049 | 6/1994 | Smith et al. | 514/772.6 |
| 5,674,514 | 10/1997 | Haesslin | 424/405 |
| 5,747,022 | 5/1998 | Slavcheff | 424/78.03 |

FOREIGN PATENT DOCUMENTS

| | | | |
|---|---|---|---|
| 10992/92 | 1/1993 | Australia | A01N 25/04 |
| 0 111 580 | 6/1984 | European Pat. Off. | A01N 25/04 |
| 0 589 838 A1 | 3/1994 | European Pat. Off. | A01N 25/04 |
| 2 699 426 | 6/1994 | France | B01F 17/52 |
| 33 04 457 | 10/1983 | Germany | A01N 25/04 |
| WO 89/03175 | 4/1989 | WIPO | A01N 25/04 |
| WO 91/14365 | 10/1991 | WIPO . | |

OTHER PUBLICATIONS

International Search Report (Jan. 2, 1995) PCT/GB94/02014.
Database WPIDS, Week (9249) London: Derwent Publications Ltd., AN–92 400848, Class A96, EP516508, (SLAU–N) Abstract.
Database WPIDS, Week 9321, London: Derwent Publications Ltd., AN–93–171949, Class A25, JP 05–103969–A, (Lion Corp) Abstract.

Primary Examiner—Richard D. Lovering
Assistant Examiner—Daniel S. Metzmaier
Attorney, Agent, or Firm—David R. Crichton

[57] ABSTRACT

An oil in water emulsion comprises a continuous aqueous phase and a discontinuous oil phase which is either a hydrophobic liquid which is immiscible with the aqueous phase or is a solid phase obtained by providing an emulsion in the aqueous phase of a solution of potentially solid material in the hydrophobic liquid and converting this solution to a solid phase, and the emulsion is stabilized by the inclusion of water-soluble stabilizing polymer in the aqueous phase and oil solubilizing stabilizing material, generally polymer, in the oil phase. The or each polymer is preferably a copolymer of hydrophilic and hydrophobic groups, preferably being formed by copolymerization of water-soluble monomer and oil-soluble monomer that provide the desired groups in the polymer without further reaction. Partially hydrolyzed polyvinyl alcohol can be used as the water-soluble polymer.

13 Claims, No Drawings

STABILIZATION AND USE OF HETEROGENEOUS LIQUID COMPOSITIONS

This application is filed under 35 U.S.C. 371 and based on PCT/GB 94/02014, filed Sep. 15, 1994.

This invention relates to compositions that are generally referred to as oil-in-water emulsions. These are; storage-stable, heterogeneous, liquid compositions comprising a continuous aqueous phase (the "water") and a discontinuous dispersed phase of a hydrophobic liquid (the "oil") which is immiscible in the water. Instead of the dispersed phase being a liquid, it can be a solid obtained by providing an emulsion in the water of a solution in the oil of potentially solid material, and then converting this solution to a solid phase while it is emulsified in the water.

BACKGROUND OF THE INVENTION

It is standard practice to include various additives in such emulsions in order to facilitate their initial formation and to promote stability, in particular by reducing coalescence. Thus it is conventional to include one or more emulsifiers or surfactants. The use of combinations of emulsifiers of different HLB values is conventional. The use of two surfactants that are intended to react with one another is described in U.S. Pat. No. 4,472,291. The particle size in this is below 0.5 μm.

Conventional emulsifiers consist of a single hydrophobic moiety and a single hydrophilic moiety (for instance an ethoxylated fatty alcohol consists of a fatty alkyl hydrophobic group and a hydroxy-terminated polyoxy ethylene hydrophilic group). However emulsifiers that have a more complex structure are known for specialised purposes.

For instance it is known from GB 2,001,083, GB 2,002,400 and EP 333501 to provide an oil-soluble emulsifier by condensing hydroxy stearic acid with itself and on to polyethylene glycol or polyethylene imine. The resultant product may contain molecules having a polyoxyethylene or polyethylene imine backbone terminated at each end by an end group containing a stearic group or a condensate of several stearic groups, thus providing terminal hydrophobes and a central hydrophilic chain. We have used these oil-soluble materials dissolved in the continuous phase of water-in-oil emulsions and suspensions.

It is also to known to use block copolymers of ethylene oxide and propylene oxide and/or butylene oxide as emulsifiers. We believe that existing emulsification systems always require, as an essential ingredient, the use of a conventional emulsifier of the type having a single hydrophobic moiety and a single hydrophilic moiety. Such emulsifiers are thought to be effective at promoting stability as a result of this single hydrophobic moiety being physically attracted into the oil phase and a single hydrophilic moiety being physically attracted into the water phase.

The emulsifiers and surfactants concentrate at the interface between the two phases, but it is also known that emulsion properties can be altered by viscosifying the water phase. Thus a water-soluble polymer that is wholly hydrophilic, for instance high molecular weight polyacrylic acid, can be distributed throughout the water phase in order to viscosity it.

It is known from, for instance, EP 126528 to provide an emulsion in oil of aqueous polymer droplets (i.e., a water-in-oil emulsion) wherein the formation of the emulsion is promoted by the use of a conventional water-in-oil emulsifier (e.g., sorbitan mono oleate) and the stability of the emulsion is promoted by an oil-soluble stabilising polymer dissolved in the continuous oil phase. This polymer can be formed by copolymerisation of water insoluble ethylenically unsaturated monomer (for instance stearyl methacrylate) with ethylenically unsaturated carboxylic acid (for instance methacrylic acid) or it can be, for instance, a polyethylene glycol-polyhydroxy stearic acid condensation product as mentioned above.

It is also known to make water-in-oil-in-water emulsions using different polymers having different solubilities. For instance an oil-soluble material described as a Polaxamer surfactant of high molecular weight is incorporated in the oil phase and a water-soluble polymer such as polyacrylic acid is incorporated in the water phase in the system described in Chemical Abstracts 105(2)11999 V.

Various other high molecular weight surfactants have been proposed in the literature for various uses, for instance in JP-a-5103969 and in EP-A-516508.

By use of conventional emulsifiers having a single hydrophile and a single hydrophobe it is often possible to make reasonably stable oil-in-water emulsions from a wide range of aqueous and hydrophobic liquids. If inadequate emulsifier is used, the heterogeneous composition will not be a stable emulsion but will instead coalesce and may break. Increasing the amount of conventional emulsifier having single hydrophobe and single hydrophile tends to result in reduced particle size and increased emulsion stability. However this reduced particle size is not always, in itself, a desirable result because the resulting rheology may then be unsatisfactory, especially when the amount of continuous phase is rather low, for instance being less (on a weight basis) than the amount of continuous water phase.

As an example, we have attempted to make an emulsion in water of a solution in oil of chlorpyrifos wherein the amount of oil phase (a solution in oil of chlorpyrifos) is more than the amount of water phase. We have found that at these high concentrations of chlorpyrifos and oil it is necessary significantly to increase the amount of conventional emulsifier to such an extent that the particle size is then very low (for instance below 0.2 μm) and the resultant composition has an unacceptable rheology that is like a paste and which is difficult to mix into water.

Another disadvantage associated with increasing the amount of emulsifier is that some of the emulsifiers that would normally be considered to be suitable (for instance containing a single hydrophobe and a single hydrophilic group) are sometimes alleged to have undesirable environmental effects, for instance inadequate biodegradation or foaming properties. It is therefore desirable to minimise the amount of these.

We have observed that with conventional emulsions, on storage they have a reasonably wide particle size distribution (for instance less than 50% by weight of the particles having a size within 50% of the average particle size). Usually the distribution is bimodal, especially after storage. We have also observed that the average particle size tends to increase significantly (for instance by 50% or more) on storage even when the composition may appear storage stable, and that the particle size distribution may also increase on storage.

Oil-in-water emulsions having agricultural ingredient in the oil phase are desribed in WO89/03175. These include a surfactant in the aqueous phase and the surfactants listed are described as, for instance, ethoxylated alcohols, anionic/non-ionic blends, block copolymers, non-ionic ethoxylated alcohols and other types. It is stated that the inclusion of an aqueous latex can substantially stabilise the emulsion. It is stated that the latex combines with oil droplets of the emulsion to produce a substantial number of particles with a size between the emulsion droplets and the size of the latex particles. Equilibration between the latex particles and the emulsion droplets is said to occur, and so the stabilised emulsion presumably has the polymer of the latex in the oil droplets. Suitable polymers are said to include polystyrene, styrene butadiene polymers, styrene butyl polymers, polyvinyl acetate, vinyl acetate ethylene polymers, acrylic styrene polymers and acrylic copolymers. The oil phase into which the polymer is said to equilibrate can be selected from materials such as aromatic hydrocarbons, mineral oils, kerosene, polybutene, certain amides or esters and chlorinated hydrocarbons.

Existing systems of stabilising oil-in-water emulsions still leave room for improvement, especially when it is desired to have a relatively high amount of the emulsified oil phase in the emulsion and/or a relatively high amount of active ingredient dissolved in the oil phase. It would be desirable to be able to provide improved stabilisation of such emulsions using readily available materials and in particular materials that very cost-effective and readily available.

DETAILED DESCRIPTION OF THE INVENTION

According to the invention, an oil-in-water emulsion comprises a continuous water phase of aqueous liquid and
a discontinuous oil phase which is either a hydrophobic liquid which is immiscible with the aqueous liquid or is a solid phase obtained by providing an emulsion in the aqueous phase of a solution of potentially solid material in the hydrophobic liquid and converting this solution to a solid phase, and the emulsion is stabilised by
a water-soluble stabilising material in the aqueous liquid and oil-soluble stabilising material in the oil phase,
and in this emulsion the water-soluble stabilising material is a water-soluble stabilising polymer which is dissolved in and is preferentially soluble in the aqueous liquid.

The oil phase can include dissolved (or dispersed) material additional to the oil-soluble stabiliser and any active ingredient that is in the oil phase, but preferably does not include an emulsified water phase since this invention is primarily concerned with two-phase oil-in-water emulsions.

The discontinuous phase of the oil-in-water emulsions of the invention must have small dimensions in order that the product is an emulsion. The discontinuous phase can be a microemulsion having a very small particle size in which event the particles can have a very small size (e.g., below 0.1 $\mu$m) in one direction and can be longer in the other direction, for instance tending towards a filamentary network in which there may appear to be some interconnection. Preferably however the discontinuous phase is an emulsified phase of discrete particles having the same shape as is conventional for emulsions, namely a substantially spherical shape. The particle size of such emulsions should be below 10 $\mu$m and frequently is below 5 $\mu$m. Although the stabilisation systems of the invention can be applied to particulate microemulsions, for instance down to 0.01 $\mu$m, these microemulsions can incur disadvantages associated with, for instance, the energy required for their production and/or the rheology of the final compositions, especially if the concentration of dispersed phase is high. Accordingly generally the particle size is above 0.01 $\mu$m and usually it is above 0.5 $\mu$m. Particle sizes in the range 0.5 to 5, preferably around 1 to 3, $\mu$m are generally preferred.

All particle sizes mentioned herein are average particle size measured by laser light scattering techniques such as Malvern Mastersizer Model 1002. The sizes mentioned above are the initial sizes that exist when the particle size is measured as soon as practicable (e.g., within an hour or so) after manufacture.

We have found that improved emulsions are obtained if the particle size distribution is narrower than in conventional emulsions and if the change in particle size on storage is lower than in conventional emulsions.

Preferred emulsions have an initial particle size below 10 $\mu$m, preferably below 5 $\mu$m, and the particle size after one week, and preferably one month, at 54° C. is 1 to 1.5 times, preferably 1 to 1.1 or 1.2 times, the initial particle size.

Preferred emulsions have a particle size distribution that is not bimodal but is Gaussian and preferably at least 70% by weight of the particles have a size within 50% of the average particle size both initially and after storage at 54° C. for at least a week, preferably a month. Preferably at least 90% by weight are within 67% of the average.

The emulsions stabilised by the defined stabilisers and preferably having the defined particle size distribution and/or the defined change in particle size distribution on storage are new materials that give significantly improved stability, especially when the amount of water phase is relatively low.

The water-soluble polymer must be preferentially soluble in the aqueous liquid so that the amount of water-soluble polymer that is dissolved in the oil is very low. Preferably the water soluble polymer is substantially insoluble in the oil. Conversely, the oil-soluble polymer must be preferentially soluble or dispersible in the oil so that the amount that dissolves into the water is very low, and preferably the oil-soluble polymer is substantially insoluble in water.

When referring to solubility of the polymer, we refer to the solubility of the polymer that is supplied for use in the emulsion in the respective phase of the emulsion in the absence of the other phase. For instance the solubility in water of the water-soluble polymer must be such that the supplied polymer dissolves in the component that is to provide the aqueous phase. Thus if the aqueous phase is alkaline during use then the solubility should be determined in that alkaline phase and in the absence of the oil.

It is preferred that the water-soluble polymer should include a plurality of groups which are chemically or physically attracted to the oil phase. Best results appear to occur when there are a large number of the groups so as to provide multiple anchoring sites at the interface. Preferably there are a plurality of the hydrophilic and hydrophobic groups recurring along the chain, instead of having a concentration of one type of group at the centre and a concentration of the other type at each end of the polymer chain.

Preferably the water soluble polymer is formed of a plurality of recurring hydrophilic groups and recurring hydrophobic groups, wherein the types and amounts of hydrophilic groups and hydrophobic groups are sufficient to render the polymer soluble in water. Preferably the polymer has a polymeric backbone with a plurality of hydrophilic and hydrophobic units recurring substantially uniformly along its backbone. In particular it is preferred that the water soluble polymer is a polymer formed by copolymerisation of water-soluble monomer and water-insoluble oil-soluble monomer. Preferably the water-soluble monomer is free of polyethoxy groups, as described below, and preferably has molecular weight below 500 as described below. Instead of forming the water-soluble polymer by copolymerisation of the monomers that provide the desired hydrophilic and hydrophobic groups, it is also possible to use as the water-soluble polymer partially hydrolysed polyvinyl alcohol.

Known oil-soluble stabilising materials can be used, such as sorbitan mono-oleate or other conventional oil-soluble surfactants that are used in oil-in-water emulsion. Preferably, however, oil-soluble stabilising polymer is used. This is dissolved in or dispersed in the hydrophobic liquid and should be preferentially soluble in the hydrophobic liquid.

Preferred compositions of the invention have the particles of the emulsion coated with a substantially continuous film of polymeric material, this film being formed by the concentration at the interface of water-soluble and water-insoluble polymers that are, at the interface, sufficiently compatible to form a continuous film. Accordingly the polymers should be film-forming and should be chemically and physically compatible such that they will form a continuous film at the interface. Because this film is formed both from oil-soluble and water-soluble polymer it provides good stabilisation. The film is more homogeneous than the layer obtained using conventional emulsifiers. The film can be sufficiently homogeneous as to act as a protective film that, when the active ingredient can react with water, helps protect active ingredient in the oil phase from the chemical deactivation that can occur upon exposure of the active ingredient to water. Thus enhanced chemical stability can also be obtained by the invention for active ingredients that are chemically unstable in contact with water.

Preferably the oil-soluble stabilising polymer includes a plurality of groups which are chemically or physically attracted to the water phase. Although it is possible to obtain some benefit when the oil-soluble polymer contains very few groups attracted to the water phase (and/or the when the water-soluble polymer includes very few groups attracted to the oil phase) best results appear to occur when the oil-soluble polymer has a large number of groups attracted to the aqueous phase. Preferably therefore the oil-soluble polymer also is formed of a plurality of hydrophilic and hydrophobic groups recurring along the chain, instead of having a concentration of one type of group at the centre and a concentration of the other type of group at each end of the polymer chain. Preferably the oil-soluble polymer is formed of a plurality of recurring hydrophilic and hydrophobic groups wherein the types and amounts of the hydrophilic and hydrophobic groups are sufficient to render the polymer preferentially soluble in water. Preferably the polymer has a polymeric backbone with a plurality of hydrophilic and hydrophobic units recurring substantially uniformly along its backbone.

When using a stabilising polymer in the invention which has hydrophilic and hydrophobic units recurring substantially uniformly along the backbone, the distribution can be as a block copolymer and thus it is possible to use, as either our both of the stabilising polymers, a polymer that is a copolymer of ethylene oxide with propylene oxide and/or butylene oxide. The copolymer is generally a block copolymer having recurring ethylene oxide blocks and recurring propylene and/or butylene oxide blocks. The ethylene oxide units or blocks act as hydrophilic units while the other units or blocks act as hydrophobic units. By selecting the proportions of ethylene oxide units on the one hand and propylene oxide/butylene oxide units on the other it is possible to provide polymers which are either oil soluble but which have ethylene oxide hydrophilic linkages that are attracted to the aqueous phase, or polymers which are water soluble but which have propylene oxide/butylene oxide linkages which are attracted to the oil phase. Materials of this type are sold under the trade name Pluronic.

The number of each type of recurring groups can be quite low when the polymer is a block copolymer, e.g., 5, or more, usually 10, or more but preferably there are many more so as to increase the number of anchoring sites. Typically there are above 30, often above 50, of each type of group. In particular best results are obtained when the groups in either (and preferably both) polymer are alternating or random copolymers in the sense that the units are substantially uniformly distributed along the length of the chain with no deliberate formation of blocks of units within the chain. This allows maximization of the number of anchoring sites while maintaining the desired solubility.

Preferably the water-soluble stabilising polymer (and preferably each of the stabilising polymers) is made by addition polymerisation of ethylenically unsaturated monomers, so that the or each polymer has a hydrocarbon backbone carrying pendant groups that provide its hydrophilic and hydrophobic properties. Preferably the hydrophilic groups are introduced as water-soluble monomer and the hydrophobic groups are introduced as oil-soluble monomer.

The water-soluble monomer or monomers preferably have a solubility in deionised water at 20° C. of at least 10, and usually at least 50, grams in 100 grams water. The oil-soluble monomer or monomers preferably has a solubility in deionised water at 20° C. of below 10 grams and generally below 5 grams, in 100 grams water.

In use it is desirable that each polymer should concentrate at the interface between the two phases and this can be promoted by appropriate choice of the hydrophilic and hydrophobic groups, and in particular by appropriate choice of the hydrophilic and hydrophobic comonomers and their proportions. Each polymer at the interface will tend to provide multiple anchoring points at the interface and so the use of polymers having a plurality of recurring groups which are attracted to the opposite phase will optimise the provision of multiple anchoring locations from each side of the interface. As a result, this optimises the interaction between the two phases and thereby achieves increased stability.

The interaction can rely solely upon physical effects. For instance hydrophilic pendant groups in an oil-soluble hydrophobic polymer will tend to extend from the oil phase into the water phase, and hydrophobic groups in a water-soluble polymer will tend to extend from the water phase into the oil phase. Accordingly the invention includes the use of polymers that achieve their stabilising effect in this manner.

When the polymer is an addition polymer of ethylenically unsaturated monomers, the monomers may be acrylic (including methacrylic), allylic or other vinyl monomers.

Suitable oil-soluble, water-insoluble monomers include alkyl (meth) acrylates, styrene, alkyl styrenes, vinyl esters, vinyl halides and acrylonitrile. It is particularly preferred for the insoluble monomers to comprise alkyl (meth) acrylates. The alkyl group frequently is C1–4 alkyl when the insoluble monomer is to be incorporated into a water-soluble polymer but higher alkyl (meth) acrylates are generally used as part or all of the insoluble monomer for incorporation in oil-soluble polymer. For instance C8–C24 alkyl acrylate or, more usually, methacrylate is preferably incorporated into water-insoluble polymer.

Suitable water-soluble monomers include ethylenically unsaturated carboxylic acids and their water-soluble salts, (meth) acrylamide, and hydroxy alkyl esters of ethylenically unsaturated carboxylic acids and ethylenically unsaturated phosphates, sulphonates and amines and other conventional water-soluble monomers. Suitable amine monomers are dialkylaminoalkyl (meth)-acrylates and -acrylamides.

The carboxylic acid monomers are generally in water-soluble salt form in water-soluble polymer and in free acid in water-insoluble polymer. Similarly the amino groups are usually present in free base form in the oil-soluble polymers and in quaternary or acid addition salt form in the water-soluble polymers.

The proportions of each type of monomer are selected to give the desired solubility in the relevant phase. Generally the amount of hydrophilic monomer is in the range 5 to 80% molar, with the balance being hydrophobic.

Instead of or in addition to incorporating the entire pendant group into the polymer during initial polymerisation, it can be added by post-reaction but this is less preferred. For instance polyethylene glycol can be reacted on to carboxylic acid groups in a pre-formed polymer to provide recurring pendant groups of the formula AnOH where A represents $CH_2CH_2O$, where n is an integer, and corresponding compounds in which the final hydroxyl group can be replaced by, for instance, methoxy. The preformed polymer can be, for example, a copolymer of (meth) acrylic acid and alkyl (meth) acrylate on to which polyethylene glycol can be reacted. Alternatively, the pendant group AnOH can be incorporated during initial polymerisation by use of an ester of polyethylene glycol and (meth) acrylic acid.

It is also possible to incorporate long chain pendant hydrophobic groups during initial polymerisation such that the polymer is then similar to the polymers known as associative polymers (for instance available from Allied Colloids Limited under the trade name Rheovis) but the polymer and its amounts should be such as to avoid major viscosification. Such polymers are water soluble (in aqueous alkali) but have recurring hydrophobic groups pendant to the chain. These hydrophobic groups can be, for instance, C8–30 aliphatic or aromatic hydrocarbon groups bonded direct to the chain or through a carboxylic linkage. Preferably they comprise such C8–30 groups on a polyethylene oxide chain so that the pendant group has the formula AnR where A represents $CH_2CH_2O$, n is 2–100 and R is C8–30 aliphatic or aromatic. n is generally 10 to 30 and R is generally C8–24 alkyl or alkaryl or aralkyl.

Although it is possible to use post-reacted polymers or associative or other polymers having polyethoxy pendant groups, it is greatly preferred (for instance for reasons of availability, effectiveness, cost and simplicity) to use polymers in which the polymers and the monomers have conventional short pendant groups, such as are provided by the monomers listed above. Thus preferably the monomers are free of polyethoxy linkages, and in particular the water-soluble monomers are preferably free of polyethoxy linkages. The monomers, and especially the water-soluble monomers, preferably have molecular weight below 500 and often below 250, and usually below 150 for anionic or non-ionic monomers.

Instead of forming the polymer by copolymerisation of monomers which directly provide the desired end groups it is also possible to provide the monomer by, for instance, hydrolysis of some of the pendant groups in a polymer, e.g., by partial hydrolysis of polyvinyl acetate, for instance to 50 to 90% hydrolysis, or even to 95% hydrolysis. We refer to this as partially hydrolysed polyvinyl alcohol.

Although best results are generally achieved when using two polymers formed by copolymerisation of hydrophilic and hydrophobic groups, it is also possible for at least one of the polymers to be a natural polymer or a polymer of simpler construction, although it is again preferred that the polymer should have solubility such that it will concentrate at the interface. For example water-soluble polymers that can be used to some extent in the invention include starches, celluloses and polyvinyl alcohol.

The preferred combination of stabilisers is the use of a water-soluble copolymer formed by copolymerisation of water-soluble and water-insoluble (oil-soluble) monomers that provide the desired hydrophilic and hydrophobic groups (or partially hydrolysed polyvinyl alcohol) and an oil-soluble polymeric stabiliser which is formed from hydrophilic and hydrophobic monomers, and wherein the hydrophilic and hydrophobic groups are regularly and randomly distributed along the polymer backbone (i.e., excluding block copolymers).

Another preferred combination uses a water-soluble addition copolymer of recurring hydrophilic and hydrophobic groups as before, together with an oil-soluble polymer that is a block copolymer of hydrophilic and hydrophobic blocks (generally ethylene oxide and propylene oxide) or a condensate of hydrophobic end groups on to a hydrophilic backbone.

Although satisfactory results can be obtained by reliance solely on the physical attraction between the polymer in one phase and the hydrophilic or hydrophobic properties of the other phase (including the polymer in that phase), it is particularly preferred in the invention to rely upon chemical attraction between polymer in one phase and the other phase. This attraction can be between the polymer and the bulk liquid in the other phase or between the polymers in the two phases.

In particular, it is preferred that at least one of the polymers should include pendant groups that can exist in ionised or non-ionised form wherein the solubility of the ethylenically unsaturated monomer containing the non-ionised groups is much greater in oil and much less in water than the solubility of the corresponding monomer containing ionised groups.

In particular, it is preferred that the oil-soluble polymer should include tertiary amine or carboxylic acid groups. The carboxylic acid groups may be converted to ammonium or sodium or other alkali metal salt form and the tertiary amine groups may be converted to quaternary ammonium or hydrogen halide salt form.

It is sometimes satisfactory to rely upon alkali or amine dissolved in the water phase to provide this conversion within the dispersion, in which event the oil-soluble polymer may be a copolymer of water-insoluble ethylenically unsaturated monomer with ionisable ethylenically unsaturated monomer and the water soluble polymer may be a copolymer of any convenient blend of water-soluble and water-insoluble monomers. Preferably, however, the water-soluble polymer includes ionised groups carrying ions that can ionise the ionisable groups in the oil-soluble polymer.

In preferred compositions of the invention, the water-insoluble polymer is a polymer of ethylenically unsaturated carboxylic acid or ethylenically unsaturated tertiary amine groups (in unionised form), copolymerised with alkyl (meth) acrylate or other water-insoluble oil-soluble monomer or monomers, and the water-soluble polymer is a copolymer of water-insoluble monomer and water-soluble monomer which is, respectively, ethylenically unsaturated carboxylic acid salt or tertiary amine hydrogen halide or quaternary ammonium salt.

In the combination using carboxylic groups, it seems that the free acid groups provided at the interface by the oil-soluble polymer are partially ionised by the ions from the water-soluble polymer (or from the water phase) so as to render the oil-soluble polymer more soluble in water and less soluble in oil. The ionised carboxylic groups in the water-soluble polymer are preferably partially converted to the free acid form by ion exchange at the interface with the free carboxylic groups from the oil-soluble polymer, thereby rendering the water-soluble polymer less soluble in water. A similar mechanism will occur for polymers containing tertiary amino groups in the oil-soluble polymer and quaternary ammonium or hydrogen halide addition salts in the water-soluble polymer.

The preferred oil-soluble polymer stabilisers for use in the invention are copolymers of (meth) acrylic acid (as free acid) or other carboxylic acid monomer with insoluble monomer which is preferably fatty alkyl (meth) acrylate, most preferably copolymers of methacrylic acid and C12–24 alkyl methacrylate, optionally copolymerised with other water-insoluble monomers such as styrene or alkyl methacrylates. The amount of methacrylic acid or other free acid in the monomers is generally from 0.1 to 0.8, often around 0.25 to 0.4, moles per mole of polymer.

Preferred water soluble polymers for use in the invention are polyvinyl alcohol or copolymers of (meth) acrylic acid ammonium, sodium or other water-soluble salt with alkyl (meth) acrylate (wherein the alkyl is generally C1–4 alkyl, usually methyl or ethyl) and/or styrene or other suitable insoluble monomer, optionally blended with other soluble monomer such as acrylamide. The amount of acid is generally 0.08 to 0.8 moles per mole polymer.

Another way of ensuring good concentration of the stabilising polymers at the interface is to use polymers that chemically interact. For instance if one polymer is anionic and the other is cationic they will tend to form a complex at the interface. As an example, an anionic water-soluble polymer (as sodium salt or free acid) will tend to form a complex with a cationic oil-soluble polymer (as free tertiary amine or as quaternary ammonium or hydrogen halide salt).

The molecular weight of the water soluble polymer is preferably quite low, for instance being in the range 1,000 to 1 million, typically 10,000 to 100,000. Preferably the water-soluble polymer and its amount are such that the use of the water-soluble polymer does not result in significant increase in the viscosity of the aqueous phase.

Typically the molecular weight of the oil-soluble polymer is in the range 10,000 to 1 million. Typically the oil-soluble polymer gives a solution viscosity in the range 5 to 20,000 cps when measured at 20° C. using a Brookfield viscometer.

The preferred polymers are substantially linear polymers and in particular it is preferred that the materials from which they are made should not include any significant content (e.g., a deliberate addition) of a cross-linking agent or any other material that will tend to cause the formation of a cross-linked or other bulky, non-linear, molecule.

The polymers may each be made by polymerisation in conventional manner. For instance water-soluble polymer can be made by aqueous solution (including gel) polymerisation or by reverse phase emulsion or bead polymerisation, in conventional manner. The oil-soluble polymer can be made by organic solvent polymerisation but more usually is provided as latex made by oil-in-water emulsion polymerisation.

Suitable amounts of each stabiliser will depend upon the content and amount of the water and oil phases and on the particular polymers that are being used.

The amount of water-soluble polymer is generally at least 1% and usually at least 2% by weight of the total emulsion, but is usually not more than 12% and is preferably below 5% by weight. Based on the water phase, the amount of water-soluble polymer is often at least 3% and usually at least 5%. It may be up to 20% but is usually below 15%, by weight of the aqueous phase.

The amount of the oil-soluble polymer is generally at least 0.3% and is frequently at least 1% by weight of the total emulsion. It may be up to around 10% but generally is not more than about 5% by weight of the total emulsion. Based on the weight of the oil phase, the amount of the oil-soluble polymer is often at least 0.5% and usually at least 1.5%. It may be up to around 15% but is usually not more than around 8% by weight.

The amount of water-soluble polymer (by weight) is generally 0.5 to 10 times, frequently around 1 to 5 times, the weight of oil-soluble polymer.

The emulsion may be made in conventional manner by combining the various components of the emulsion in any convenient and conventional manner. The preferred way of making the compositions of the invention is to preform each of the phases, including the desired polymeric stabiliser for that phase, and then to add gradually with stirring the dispersed phase to the phase that is to be the continuous phase. Stirring can be a Silverson mixer or other suitable homogeniser or rapid agitator.

At least 33% by weight, generally at least 50% and preferably at least 66% by weight of the continuous aqueous phase (i.e., excluding the oil phase) is generally water. The amount of water can be as much as, for instance, 98% but usually is below 90% by weight of the aqueous phase. The aqueous phase often includes an alcohol or a glycol in order to modify the properties of the composition, and in particular to impart anti-freeze characteristics. For example the composition may contain up to 25% by weight of an alkylene glycol, generally propylene glycol or ethylene glycol, as anti-freeze. Other components that can be included in the continuous aqueous phase (apart from the polymeric stabiliser) include conventional viscosifiers.

The normal reason for providing an oil-in-water emulsion is to provide a means of delivering the oil phase to a desired location, and so the oil phase normally contains or consists of a commercially useful material that may be referred to as an active ingredient. If the active ingredient is an oil then the oil phase may consist solely of this active ingredient (together with polymeric stabiliser). Often, however, the oil phase is a solution of an oil-soluble active ingredient in an organic solvent, the resultant solution being hydrophobic and serving as an oil phase. Suitable organic solvents for this purpose are hydrocarbon liquids, other hydrophobic solvents, liquid diester solvents, cyclohexanone, dibutyl phthalate and other conventional vehicles in which oil-soluble active ingredients can be dissolved or dispersed. Generally the oil phase consists of the active ingredient alone or the active ingredient and solvent, together with the oil-soluble stabilising polymer. Other components can be included if desired in order to modify the properties, in known manner. The oil phase is normally free of water.

It is also possible to form an oil-in-water emulsion in which the oil phase is a solution of potentially solid material in an organic solvent and then to remove the organic solvent, so as to leave a solid dispersed phase. The removal of the organic solvent is usually by distillation, frequently by the process which is commercially referred to as azeotropic distillation (even though a true azeotrope may not be formed), in which event the organic solvent generally needs to be more volatile than the water.

As mentioned, either or both of the water and oil phases may include other additives and thus it is possible to include a conventional emulsifier, for instance having either one or two hydrophilic groups and one or two hydrophobic groups, in either or both phases. However it is an important advantage of the invention that the emulsions can be, and preferably are, formed in the absence of water-soluble emulsifier or surfactant. If such a surfactant is present, its amount is generally, on a weight basis, less than the amount of water-soluble stabilising polymer and usually it is less than half the amount of water-soluble stabilising polymer.

As indicated, it is possible to use oil-soluble surfactant in the absence of oil-soluble polymer but preferably oil-soluble polymer, most preferably a polymer containing hydrophilic and hydrophobic groups as described above, is used as some or all of the stabiliser. Under these circumstances, it is preferred that the emulsion is formed in the absence of oil-soluble emulsifier or surfactant, but if such material is present its amount is generally less than the amount of oil-soluble polymer, and usually it is less than half the amount of oil-soluble polymer (by weight).

Usually the total amount of non-polymeric surfactants and emulsifiers is below 2%, generally below 1% and preferably below 0.5% by weight of the total emulsion, and preferably the emulsion is substantially free of such emulsifiers. Preferably the only additives which are present to have a surface effect at the interface are the defined polymers, and in particular are preferably the defined copolymers of ethylenically unsaturated hydrophilic monomers and hydrophobic monomers, most preferably (meth) acrylic acid and alkyl (meth) acrylates and/or styrene.

The amount of the emulsified oil phase, by weight based on the weight of the total emulsion, is normally at least 30%. Since an advantage of the invention is that it is possible to obtain very high amounts of oil phase, the amount is usually at least 40% and generally at least 50% by weight. Amounts of at least 60% can be achieved, for instance up to 70% or even 75%. With normal emulsifying systems, it is not possible to include such large amounts of oil phase in the emulsion without incurring a substantial risk of the emulsion breaking, with some or all of the oil particles coalescing to form an oily layer and/or a water-in-oil emulsion either throughout the system or as an upper layer.

Preferred compositions of the invention are oil-in-water emulsions substantially free of conventional emulsifier and stabilised by the polymers described above, especially the linear addition copolymers containing carboxylic groups, wherein the average particle size is around 0.5 to 3 $\mu$m, the amount of oil phase is at least 40% by weight, generally around 50 to 65 or 70% by weight, and the average particle size after 7 days storage at 54° C. is 1 to 1.2 times the initial average particle size, and the particle size distribution initially and on storage is preferably narrow, as described above.

Suitable active ingredients that may be in the liquid phase include water-insoluble materials which are either oils or are soluble in oils and include materials such as fragrances, pesticides, paper sizes and moisturising oils (e.g., for cosmetics). When the material is liquid, it can be used without a solvent, but when it is solid it is incorporated as a solution. It is generally desirable to maximise the concentration of active ingredient in the oil phase by minimising the amount of solvent and typically the concentration of active ingredient is at least 30 to 40%, and usually at least 50%, by weight of the oil phase. It can be up to, for instance, 70 or 75% or higher, for instance when the active ingredient is a liquid or a material that can form a solution upon admixture with a very small amount of solvent. The amount of active ingredient in the composition is generally at least 20% and preferably is as much as 50 or 60% by weight of the total composition or even more. Often it is in the range 30 to 50% by weight total composition.

Suitable paper sizes are ketene dimer sizes. By the invention it is possible for the first time to form an oil-in-water emulsion of a ketene dimer size that has a relatively high content of ketene dimer, for instance above 20% and typically at least 30%, e.g., up to 40%. Prior to the invention the maximum amount of ketene dimer that could be incorporated into a stable emulsion was generally around 10%, with "creaming" of the oil phase generally occurring if an attempt is made to incorporate larger amounts. The concentrated ketene dimer emulsion also has the advantage that it is chemically stable with substantially no chemical deactivation of the emulsion during normal storage. Accordingly the invention includes, as an important aspect, the provision of oil-in-water emulsions of reactive size, their production, and paper-making processes in which the emulsions are used. The general method of using them is to deliver the concentrated emulsion to the mill (thereby handling smaller volumes than are required in the prior art) and diluting the emulsion to the normal use concentration, typically of around 1%, and utilising this in the paper-making process in the conventional manner.

Another important aspect of the invention relates to the delivery of agricultural pesticides and other active ingredients. There is a serious problem in providing convenient formulations of water-insoluble pesticides because of the difficulty of formulating them as compositions that have a convenient high concentration but which can easily be diluted in water to form a sprayable composition.

This problem is particularly acute with compounds that tend to crystallise in concentrated organic solutions because it is then necessary to include sufficient organic diluent to prevent crystallisation and any oil-in-water emulsion of such a material would then normally only have a low concentration of it. This problem arises with, for instance, the formulation of chlorpyrifos. This can be supplied as a solution in chlorinated hydrocarbon and/or xylene but it would be desirable to provide it in a form in which it is dissolved in an organic solvent that is free of chlorinated hydrocarbon, preferably an aliphatic solvent such as an aliphatic hydrocarbon and which has a high content of chlorpyrifos. It is generally necessary to include at least 20%, for instance around 30 to 40%, of the solvent in the solution of chlorpyrifos in order to prevent crystallisation.

With normal emulsifying systems, using conventional emulsifiers, it is not possible to achieve a composition having an adequately high concentration of chlorpyrifos and which is reasonably stable except with the use of such large amounts of conventional surfactants that the particle size is about 0.10 $\mu$m and the rheology of composition is unacceptable because it is thick and creamy. Similar problems exist with the formulation of other agrochemicals and other water-insoluble active ingredients.

By the invention, it is now possible to formulate the chlorpyrifos or other agrochemical as an oil-in-water emulsion that is easily dilutable with water to form a sprayable composition and which has a high concentration of the chlorpyrifos or other agrochemical. For instance this concentration can be above 40% by weight of the total emulsion, often 45 to 50% or more. The particle size can easily be in the range 0.5 to 5 $\mu$m, preferably 1 to 3 $\mu$m.

The invention includes the provision of these agricultural concentrates and their use by dilution and spraying in the desired crop area that is to be treated. The agrochemical can be, for instance, an insecticide, fungicide, herbicide or nematocide. Particularly preferred agrochemicals are chlorpyrifos, pentanachlor, cypermethrin, chlorpropham, propham and trifluralin. Preferred agricultural compositions have an average particle size in the range 0.5 to 2.5 μm, often around 1 to 2 μm and a viscosity below 2,000 cps, often in the range 500 to 15000 cps (measured by a Brookfield viscometer).

Generally it is preferred that all emulsions of the invention have a viscosity below 2,000 cps, preferably below 1,200 cps.

The following are some examples. In these, Silverson, Malvern, Allox, Hypermer and Solvesso are trade marks.

EXAMPLE 1

An aqueous phase is formed of 44 grams water, 17 grams of a 30% solution of a water soluble polymer and 10 grams propylene glycol to serve as an antifreeze.

An oil phase is formed by dissolving 10 grams of a 20% solution of an oil-soluble polymeric stabiliser in 120 grams of an oil phase which is a mixture of 40 grams Solvesso 100 and 80 grams chlorpyrifos.

The water-soluble polymer is the ammonium salt of a copolymer of 60% ethyl acrylate, 25% methyl methacrylate and 15% methacrylic acid, and the oil-soluble polymer is a copolymer of 2 moles stearyl methacrylate with 1 mole methacrylic acid free acid, supplied as a solution in organic solvent.

The oil phase is added gradually to the aqueous phase using a Silverson mixer to give a stable low viscosity oil-in-water emulsion.

The resultant emulsion contains 480 g/l chlorpyrifos and which has a viscosity of 840 cps and a particle size of about 1.5 μm, both when initially formed and after storage for one week at 54° C. In particular, the average particle size initially was measured as 1.49 μm and the average particle size after one week storage was measured as 1.54 μm.

The particle size distribution was Gaussian, with 80% by weight within 50% of the average. When the oil-soluble polymer was omitted, the distribution after storage was bimodal with peaks at around 2 and 15 μm.

EXAMPLE 2

The process of Example 1 was repeated using different amounts (percentage by weight based on total composition) of the oil-soluble polymer (OSP) and the water-soluble polymer (WSP). When the amount of WSP was 0%, it was not possible to form a sensible oil-in-water emulsion and, instead, the product was either an unwanted water-in-oil emulsion or was a product that phase separated.

The oil-in-water emulsions were subjected to two series of tests, and the results are shown in Table 1 below.

One series of tests consisted in determining the average particle size for the initial emulsions and after storage at 54° C. for eight days and for one month. Another series of tests involved subjecting the initial emulsions to three freeze thaw cycles and then measuring the average particle size. The results are shown in Table 1 below in which the first value for each combination of polymer amounts is the average particle size (in microns) for the initial emulsion, the second value is the average size after eight days storage, the third value is the average size after one month and the fourth value (in parenthesis) is the value after three freeze thaw cycles.

All the particle size measurements are conducted using a Malvern Mastersizer model 1002 fitted with MS15 preparation tank. A sample of each is placed in a 4 oz bottle and placed in the oven at 54° C.

TABLE 1

| Amount O.S.P. | Amount of W.S.P. | | | |
|---|---|---|---|---|
| | 1% | 2% | 3% | 4% |
| 3% | 4.50 | 1.96 | 1.43 | 1.03 |
| | 4.48 | 1.96 | 1.48 | 1.23 |
| | 4.89 | 1.98 | 1.48 | 1.21 |
| | (4.60) | (1.95) | (1.49) | (1.11) |
| 2% | 3.03 | 1.81 | 1.30 | 0.92 |
| | 3.26 | 1.88 | 1.37 | 1.46 |
| | 3.47 | 1.85 | 1.36 | 1.44 |
| | (3.32) | (1.84) | (1.37) | (1.07) |
| 1% | 2.12 | 1.58 | 1.10 | 0.76 |
| | 2.50 | 1.65 | 1.50 | 1.57 |
| | 2.59 | 1.67 | 1.51 | 1.60 |
| | (2.28) | (2.64) | (1.33) | (1.46) |
| 0% | 1.96 | 1.34 | 0.94 | 0.63 |
| | 7.17 | 2.88 | 2.20 | 2.30 |
| | 12.75 | 3.16 | 2.06 | 2.88 |
| | (2.67) | (1.89) | (1.76) | (1.76) |

EXAMPLE 3

A series of compositions were formed using different amounts (dry weight based on the total composition) of different water-soluble and oil-soluble polymers. In each instance the emulsion was formed from equal amounts by weight of an oil phase (consisting of Solvesso 100 containing the oil-soluble polymer) and water phase (consisting of water containing the water-soluble polymer). In each test 2.5% of the oil-soluble polymer is dissolved in the oil and 4% of the water-soluble polymer is dissolved in water (each percentage being based on the total composition so that, for instance, the concentration of water-soluble polymer in the water was 8%).

The aqueous phase was placed in an 8oz bottle and the organic phase was added over a period of 20 to 30 seconds while mixing with a Silverson mixer on full speed. The Silverson continued to mix for a further 2 minutes while the bottle was rotated. The particle size was then measured on the initial composition and after storage for three days.

In each of the examples the amount of oil-soluble polymer was 2.5% dry weight based on the total emulsion and the amount of water-soluble polymer was 4% by weight based on the total emulsion. The initial particle size and the size after 3 days was measured.

We list below the polymer combinations that were tested and the initial and three-day particle sizes. In this list Polymer A is a copolymer of 2 moles stearic acid with 1 mole methacrylic acid as free acid, and is oil-soluble. Polymer B is a water-soluble copolymer of 60% ethyl acrylate, 25% methyl methacrylate and 15% methacrylic acid as ammonium salt. Polymers that can be used in place of polymer B are polymer C, namely a copolymer of 27% ethyl acrylate, 27% methyl acrylate, 35% methyl methacrylate and 11% acrylic acid as ammonium salt, and polymer D, namely a copolymer of 68% styrene and 32% acrylic acid as ammonium salt.

A+sodium polyacrylate—phase separation

A+butyl acrylate-sodium polyacrylate—3.31/3.85

A+Atlox 4913 (polymethacrylic acid-acrylate copolymer having pendant polyethylene glycol groups reacted on to the acid groups)—2.38/3.61

A+Atlox G5000 (polyalkylene glycol ether)—0.86/0.85

A+partially hydrolysed (87%) polyvinyl alcohol Gohsenol GLO5—2.07/2.31

A+B 1.81/2.05

Hypermer D478 (non-ionic)+B 1.25/1.21

Hypermer 2296 (non-ionic)+B 0.92/0.93

Condensate of poly 12—hydroxy stearic acid with polyethylene imine+B 1.41/1.61

A+acrylamide-diacetone acrylamide copolymer 3.71/4.39

A+polyvinyl pyrollidone 4.30/5.54

It should be emphasised that these tests may not be adequately discriminating to give a true indication of stability of compositions having desired high contents of active ingredient, but they are a useful preliminary screen from which such compositions can be selected.

EXAMPLE 4

Oil-in-water emulsions having equal amounts of oil phase and water phase were prepared containing chlorpropham and propham according to the following recipes.

|  | 1. | 2. |
|---|---|---|
| Chlorpropham (98%) | 34.29 | 34.29 |
| Propham (98.5%) | 4.67 | 4.67 |
| A (21.4% solution) | 21.64 | 28.04 |
| Solvesso 100 | 39.40 | 33.00 |
| B (30% solution) | 18.90 | 13.33 |
| Propylene Glycol | 7.50 | 7.50 |
| Water | 73.60 | 79.17 |

The organic phase was mixed using a Silverson mixer into the aqueous phase, slowly, over approx. 20 seconds and the Silverson continued mixing for 2 minutes at full speed.

The particle size was then measured using the Malvern Mastersizer Model 1002 fitted with MS 15 preparation tank.

The particle size for recipe 1 was 1.19 microns and for recipe 2 was 1.64 microns.

There was no change in particle size when both of these samples were stored at 54° C. for 21 days.

EXAMPLE 5

An oil-in-water emulsion was prepared containing chlorpropham along according to the following recipe.

| Chlorpropham (98%) | 60.00 |
|---|---|
| A (21.4% solution) | 27.75 |
| Solvesso 100 | 32.25 |
| B (30.0% solution) | 20.00 |
| Propylene glycol | 15.00 |
| Water | 45.00 |

The sample prpearation was as described in Example 4. The particle size of the product was 0.76 microns. There was no change in particle size when the sample was stored at 54° C. for 14 days.

EXAMPLE 6

An oil-in-water emulsion was prepared containing cypermethrin. The oil soluble polymer used was condensate of poly 12—hydroxy stearic acid with polyethylene imine. The sample was prepared according to the following recipe.

| Cypermethrin (92%) | 43.48 |
|---|---|
| Oil soluble polymer (60% solution) | 10.00 |
| Solvessor 100 | 16.52 |
| B (30% solution) | 26.66 |
| Propylene glycol | 15.00 |
| Water | 88.34 |

The sample preparation was as described in Example 4. The particle size of the product was 1.67 microns. There was no change in particle size when the sample was stored at 54° C. for 28 days.

EXAMPLE 7

Whilst the preferable oil soluble stabiliser is polymeric, samples can be prepared using a standard oil soluble emulsifier in the organic phase. A sample was prepared containing sorbitan mono-oleate (with no polymeric material) in the organic phase according to the following recipe.

| Cypermethrin (92%) | 43.48 |
|---|---|
| Sorbitan mono-oleate | 4.00 |
| Solvesso 100 | 22.52 |
| B (30% solution) | 20.00 |
| Propylene glycol | 15.00 |
| Water | 95.00 |

The sample preparation was as described in Example 4. The particle size of the product was 1.07 microns. There was no change in particle size when the sample was stored at 54° C. for 28 days.

EXAMPLE 8

A sample containing Fenvalerate was prepared using a similar recipe to that given in Example 7. The sample was prepared according to the following recipe.

| Fenvalerate (93%) | 42.80 |
|---|---|
| Sorbitan mono-oleate | 4.00 |
| Solvesso 100 | 13.33 |
| B (30% solution) | 13.33 |
| Propylene glycol | 15.00 |
| Water | 111.54 |

The sample preparation was as described in Example 4. The particle size of the product was 1.38 microns. There was no change in particle size when the sample was stored at 54° C. for 21 days.

EXAMPLE 9

Ketene dimer size, as a wax, was dissolved in Solvesso 100 to make a solution of 50% AKD in Solvesso 100 at 70° C. A solution of copolymer A was formed in this warm solution. The warm solution was then poured into an equal weight of an aqueous phase containing a water-soluble polymer of 89% methyl ethyl (meth) acrylate and 11% acrylic acid ammonium salt with high shear mixing (10,000 rpm) using a Silverson mixer at ambient temperature for 3 minutes.

In one example the amount of the oil-soluble polymer was 1% and the amount of water-soluble polymer was 2.9% The resultant average particle size measurement was 0.95 $\mu$m.

In another example the amount of oil-soluble polymer was 1.3% and the amount of water-soluble polymer 2.6%.

Both products contained 25% ketene dimer and could be used in conventional manner to give the same sizing performance as would be expected if the polymer had been supplied as a conventional dilute emulsion having less than 10% ketene dimer in it.

EXAMPLE 10

A cosmetic formulation was formed using Polymer A as oil-soluble polymer and polymer B as water-soluble polymer:

|  | % |  |
| --- | --- | --- |
| Stearic acid | 2.00 |  |
| Mineral Oil | 5.00 |  |
| Cetyl alcohol | 2.00 |  |
| Total polymers | 0.90 | (active) |
| Deionised water to | 100 |  |

Stearic acid, mineral oil, cetyl alcohol and the required amount of polymer A were weighed into a clean dry beaker and heated to 70° C. In a separate beaker water and polymer B were heated to 70° C. The oil phase was added to the water phase with rapid stirring, until the cream was emulsified and the temperature had dropped to about 40° C. (typically 10 minutes). The formulations were allowed to cool to room temperature, aged for 24 hours and the stability was determined at elevated temperatures (45° C.) and under freeze-thaw conditions.

| Addition level (% active) | | Freeze-Thaw | Stability |
| --- | --- | --- | --- |
| Type A | Type B | Stability | @ 45° C. |
| 0.90 | 0.00 | x | x |
| 0.78 | 0.12 | x | + |
| 0.61 | 0.19 | + | + |
| 0.43 | 0.47 | + | + |
| 0.26 | 0.64 | + | + |
| 0.00 | 0.90 | + | + |

NOTE:
+ = emulsion stable under these conditions
x = emulsion unstable under these conditions

EXAMPLE 11

Another cosmetic formulation was formed, using the same polymers:

|  | % |  |
| --- | --- | --- |
| Glyceryl tricaprate/caprylate | 21.00 |  |
| Stearic acid | 4.00 |  |
| Cetyl alcohol | 1.00 |  |
| Total polymers | 2.60 | (active) |
| Carbomer (2% solution) | 10.00 |  |
| Deionised water to | 100 |  |

Glyceryl tricaprate/caprylate, stearic acid, cetyl alcohol and the required amount of polymer A were weighed into a clean dry beaker and heated to 70° C. In a separate beaker the water, Carbomer solution and polymer B were heated to 70° C. The oil phase was added to the water phase with rapid stirring, until the cream was emulsified and the temperature had dropped to around 40° C. (typically 10 minutes). The emulsions were allowed to cool to room temperature and aged for 24 hours and then the stability was determined at elevated temperatures (45° C.) and under freeze-thaw conditions.

| Addition level (% active) | | Freeze-Thaw | Stability |
| --- | --- | --- | --- |
| Type A | Type B | Stability | @ 45° C. |
| 2.60 | 0.00 | x | x |
| 2.27 | 0.33 | + | + |
| 1.75 | 0.85 | + | + |
| 1.25 | 1.35 | + | x |
| 0.74 | 1.86 | + | x |
| 0.00 | 2.60 | + | x |

NOTE:
+ = emulsion stable under these conditions
x = emulsion unstable under these conditions

What is claimed is:

1. An oil-in-water emulsion comprising:
   a continuous phase of aqueous liquid and,
   at least 30% by weight of a discontinuous oil phase which is either hydrophobic liquid which is immiscible with the aqueous liquid or is a solid phase obtained by providing an emulsion in the aqueous liquid of a solution of potentially solid material in the hydrophobic liquid and removing the liquid to convert this solution to a solid phase,
   and the emulsion is stabilized by 1 to 12% by weight based on the aqueous phase of water-soluble stabilizing material in the aqueous liquid and 0.3 to 10% by weight of the total emulsion of oil-soluble material in the oil phase,
   wherein the water-soluble stabilizing material is a copolymer of ethylenically unsaturated carboxylic acid water-soluble salt or a quaternary ammonium or hydrogen halide addition salt of an ethylenically unsaturated amine together with water-insoluble monomer comprising $C_1$–$C_4$ alkyl(meth)acrylate and/or styrene and is dissolved in and is more soluble in the aqueous liquid than in the oil phase and
   the oil-soluble stabilizing material is a copolymer of ethylenically unsaturated carboxylic acid as free acid or ethylenically unsaturated amine as free base with insoluble monomer comprising fatty alkyl (meth) acrylate and is more soluble in the oil phase than in the aqueous liquid.

2. An emulsion according to claim 1 in which the oil-soluble polymer contains free carboxylic acid groups and the water-soluble polymer contains carboxylic acid groups in the form of alkali metal or ammonium salt.

3. An emulsion according to claim 1 in which the amount of hydrophilic groups in each polymer is 5 to 80 molar percent and the amount of hydrophobic groups in each polymer is 95 to 20 molar percent.

4. An emulsion according to claim 1 having initial particle size, and a particle size after storage for one week at 54° C., in the range 0.5 to 5 μm.

5. An emulsion according to claim 1 in which the particle size after storage for one week at 54° C. is 1 to 1.2 times the initial particle size.

6. An emulsion according to claim 1 having an initial particle size distribution, and a particle size distribution after storage for one week at 54° C., wherein at least 70% by weight of the particles have a size within 50% of the average particle size.

7. An emulsion according to claim 1 in which the amount of the oil phase is at least 40% by weight of the emulsion.

8. An emulsion according to claim 1 in which the oil phase is an active ingredient or includes an active ingredient.

9. An emulsion according to claim 8 in which the active ingredient is selected from the group consisting of paper sizes, agricultural pesticides and cosmetic formulations.

10. An emulsion according to claim 9 in which the pesticide is chlorpyrifos.

11. An emulsion according to claim 8 and which is an emulsion which contains at least 40% (based on the weight of emulsion) of pesticide dissolved in the oil phase and which has a particle size in the range 0.5 to 5 $\mu$m.

12. A method of applying an active ingredient to a crop to a area comprising providing an emulsion according to claim 1 containing in the oil phase an agricultural active ingredient, diluting the emulsion with water to form a sprayable composition, and spraying the composition on the crop area.

13. A method of forming an emulsion according to claim 1 comprising emulsifying into an aqueous phase containing the water-soluble stabilizing polymer an oil phase comprising the hydrophobic liquid in the presence of the oil-soluble stabilizing material.

* * * * *